United States Patent [19]

Macri et al.

[11] Patent Number: 5,157,455
[45] Date of Patent: Oct. 20, 1992

[54] APPARATUS FOR THE CALIBRATION AND QUALITY CONTROL OF A SPECTROPHOTOMETER

[76] Inventors: James N. Macri, 170 Sidney St., Oyster Bay, N.Y. 11771; Edward J. Cook, 105 John St., Garden City, N.Y. 11530

[21] Appl. No.: 563,648
[22] Filed: Aug. 7, 1990
[51] Int. Cl.$^5$ .................. G12B 13/00; G01N 21/59
[52] U.S. Cl. ........................... 356/243; 356/416
[58] Field of Search .......... 356/243, 408, 409, 416, 356/419, 434, 435, 436; 250/252.1 A

[56] References Cited

U.S. PATENT DOCUMENTS

| | | | |
|---|---|---|---|
| 3,762,817 | 10/1973 | Harklaw | 356/434 |
| 3,832,070 | 8/1974 | Cox | 356/243 |
| 3,942,899 | 3/1976 | Longhenry | 356/243 |
| 4,059,357 | 11/1977 | Klein | 356/243 |
| 4,892,405 | 1/1990 | Sorensen et al. | 356/434 |

Primary Examiner—F. L. Evans
Attorney, Agent, or Firm—Kenyon & Kenyon

[57] ABSTRACT

An apparatus for the calibration and quality assurance of a multichannel spectrophotometer, particularly an ELISA spectrophotometer, comprises film selectively exposed in the presence of a color to produce a series of filters having a known first color and linearly increasing optical density. The response of the spectrophotometer is measured against the known color and linearly increasing optical density. Additional filters of at least one additional color permit checking the color response of the spectrophotometer. An algorithm determines whether the response conforms to predetermined conditions. An output is produced to provide a record of the calibration and quality assurance of the spectrophotometer. The invention has particular utility for conducting calibration and quality assurance of ELISA spectrophotometers used in clinical laboratory screening for infectious diseases, such as Hepatitis B. and the AIDS viruses.

19 Claims, 7 Drawing Sheets

FIG. 2
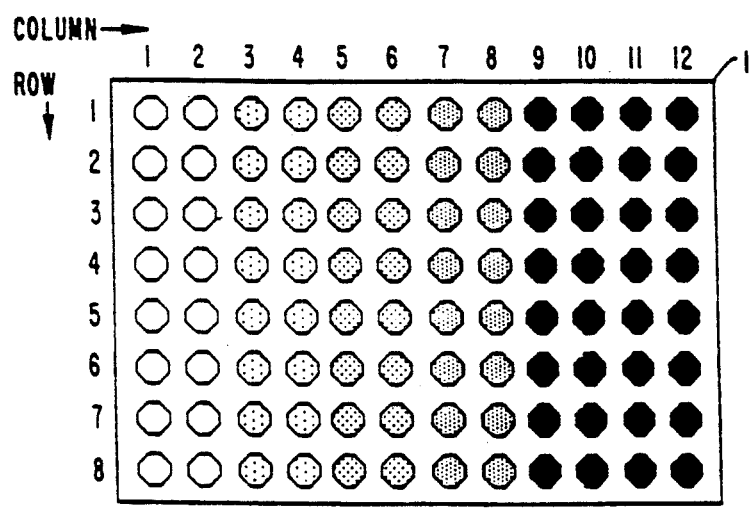
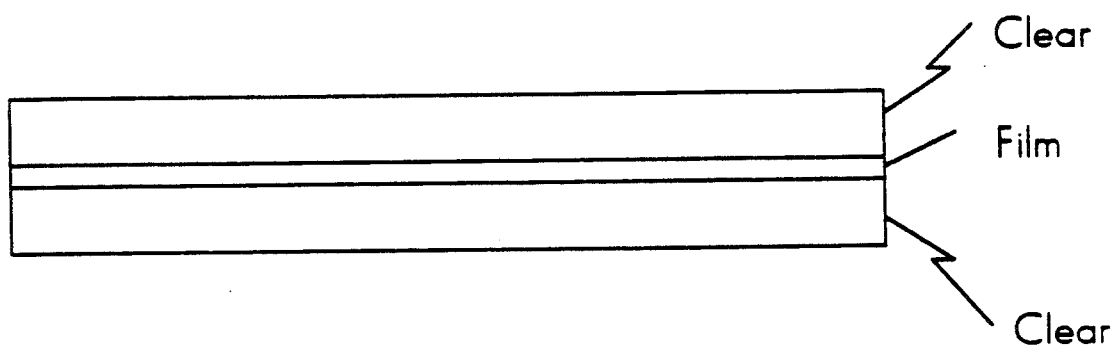
FIGURE 3

APPARATUS FOR THE CALIBRATION AND QUALITY CONTROL OF A SPECTROPHOTOMETER

BACKGROUND OF THE INVENTION

The present invention relates to an improved method and apparatus for the calibration and quality control of a spectrophotometer and particularly an ELISA spectrophotometer used in a clinical laboratory.

Spectrophotometers, including micro titer plate readers, are a well known tool in the analytical chemistry laboratory. One type of commercially available spectrophotometer is the ELISA spectrophotometer which typically comprises a plurality of light sources and detectors commonly arranged in a column of eight. The ELISA spectrophotometer can be used to analyze the photometric density produced by assay of biological materials. These assays are arranged as an assay plate having a number of columns corresponding to the number of channels of the ELISA spectrophotometer and a number of rows. Typically the ELISA spectrophotometer comprises an 8×12 matrix of 96 cells. The ELISA spectrophotometer now typically includes a microprocessor analyzing and recording the output of each channel for each assay well of a sample plate.

The ELISA spectrophotometer is a relatively recent addition to the analytical laboratory. An even more recent development has been the introduction of the ELISA spectrophotometer into the clinical laboratory. For example, the immuno-chemical identification of exposure to hepatitis B virus, the Herpes virus, and the HIV virus, and the "AIDS" virus, uses an ELISA spectrophotometer. The significance of photometric measurements made with an ELISA spectrophotometer now have implications that directly relate to the control of infectious epidemics. The measurement integrity of an ELISA spectrophotometer is therefore a matter of considerable concern to laboratory technicians, regulatory agencies and the general public.

The ELISA spectrophotometers used in clinical laboratories, however, are generally not equipped to insure proper calibration or quality control. Calibration is defined as the integrity of the normal operation of the instrument and relates to the spectrophotometer itself. Quality assurance is defined as the integrity of the results produced by a laboratory technician using a properly functioning spectrophotometer. At present, the calibration of an ELISA spectrophotometer is established once at the factory when manufactured. Generally no provision is made for confirming calibration after the spectrophotometer leaves the factory. Quality assurance is left to each individual clinical laboratory and laboratory technician.

The calibration of an ELISA spectrophotometer can be compromised through both electronic and optical errors. Electrical errors arise from a variety of causes. An ELISA spectrophotometer employs filters of predetermined density and color. An electronic mechanism selects among the filters. A failure in the selection mechanism may result in the wrong filter being inserted. A laboratory technician would not notice the malfunction even if he could view the filter.

Alternately, the electronic memory that serves the microprocessor of the ELISA spectrophotometer may fail. Such a failure would most likely remain undetected using current calibration techniques. At present, an ELISA is calibrated by "blanking" the channels to establish a base line for zero optical density. A defective memory would likely read zero during "blanking". Nothing about the reading would necessarily indicate that the ELISA was defective. A memory defect used in the context of HIV screening would preclude the production of any positive test results. Individuals exposed to a virus would test free of infection whether or not such is true.

Yet another source of electronic error is the connection between the ELISA spectrophotometer and its microprocessor. The microprocessor of a personal computer often analyzes the output of the ELISA spectrophotometer and serves as the microprocessor for the ELISA. The transmission line between the spectrophotometer and personal computer normally uses a "handshake" protocol in which the photometer generates a check sum which is then exchanged with the computer. However, most programs used to analyze the output of an ELISA spectrophotometer do not analyze the check sum. Any transmission error thus goes unrecognized.

Optical errors can originate from a number of sources. For example, dust can obstruct a channel of an ELISA spectrophotometer and thus reduce its throughput efficiency. Alternately, the light source for a particular channel may become erratic and produce "jumps" in output or "burn hot" and produce a consistently high signal. This type of erratic output cannot be corrected using baseline subtraction.

Yet another source of potential optical error involves the deterioration of the filters of the ELISA spectrophotometer. This deterioration can take many forms such as, for example, the formation of cracks. Filter deterioration which is not necessarily noticed by the human eye can nevertheless give erroneous readings.

Optical errors can produce either false positives or false negatives depending on the test being run. The resulting misdiagnosis is traumatic to the patient involved and results in a substantial expenditure of time and resources to correct.

A second type of error in an ELISA spectrophotometer measurement is human error. A filter could be improperly inserted due to any number of reasons such as improper labeling or a defective selecting mechanism. A laboratory technician also could select the wrong filter for a given measurement. In either event, the error is not readily apparent using base line substraction because the values of the baseline measurements are substantially lower than those corresponding to a sample. Inserting the wrong filter causes all samples in a particular assay to appear "normal". The purpose of the assay is compromised and individuals are again diagnosed as being free of infectious diseases whether or not such is true.

The near total absence of calibration and quality assurance controls for ELISA spectrophotometers is uncharacteristic of the clinical laboratory. Stringent governmental regulation is more the norm than the exception. These regulations typically include frequently documented calibration tests of pipettes, scales, etc. Records must also be kept documenting preventive maintenance performed on the equipment as well as identifying the equipment used to obtain the quality control and calibration measurements. For example, radiochemical procedures use stable radioisotopes in combination with the counting equipment for daily quality assurance and calibration measurements. Records are maintained for review by the appropriate government regulatory agency. Likewise, test tube immunochemical procedures employ a series of sealed test tubes having dilutions of known color for use in a one channel photometer. The quality assurance measurements and calibrations are comparable to that required for radiochemical procedures.

The quality assurance and calibration confirmation procedures employed with a single channel photometer are not adequate for more complicated clinical procedures. For example, primitive "spot-check" calibration and baseline measurements are adequate for an ELISA spectrophotometer when used in an analytical laboratory. A skilled researcher could readily determine if his equipment or his procedure were defective since he would be highly familiar with the equipment and would have some idea of what result to expect. However, the clinical laboratory technician must analyze unknown samples without intuition. Errors are not apparent. Any errors on spectrophotometric measurement become matters of public health concern rather than simply setbacks to research.

A need exists in the art for a method and apparatus for the calibration and quality assurance of ELISA and similar spectrophotometers that will work reliably and quickly in a clinical laboratory. This need was at least partially satisfied by the apparatus for the calibration and quality assurance of ELISA and similar spectrophotometers disclosed in commonly assigned U.S. Pat. No. 4,892,405. In a particular embodiment of the apparatus disclosed in U.S. Pat. No. 4,892,405, color filters are added to the wells of an ELISA sample holder. We have discovered an improved apparatus and method for the calibration and quality assurance of ELISA and similar spectrophotometers.

SUMMARY OF THE INVENTION

The present invention relates to an apparatus for the calibration and quality assurance of a multichannel spectrophotometer, particularly an ELISA spectrophotometer. The apparatus is particularly well adapted for use in a clinical laboratory which performs many repetitive tests on unknown samples. The invention allows the clinical laboratory to keep detailed records of the type normally required by governmental regulatory authorities.

The invention uses a sheet of photographic film, preferably color film with dimensions corresponding to the dimensions of an ELISA sample holder, selectively exposed in the presence of a color filter, to produce a filter or a series of filters that has/have a known first color and linearly increasing optical density. The ability of the photometer to measure this linearly increasing optical density is evaluated b comparing the measurements generated by the photometer to the known increase in optical density from filter to filter. This linearity test also ensures the alignment of the spectrophotometer. Exposure to produce an additional one or more filters of a second color permits checking the color response of the spectrophotometer. An algorithm determines whether the response follows a linear increase in the optical density of the first color and records an appropriate change in optical density using filters of the second color.

The present invention has particular applicability to ELISA spectrophotometry. The ELISA sample holder typically comprises a 8×12 matrix of 96 individual sample wells. Thus preferably the film has about the same dimensions as an ELISA sample holder and is preferably exposed to produce at least part of an 8×12 matrix corresponding to the matrix on the typical ELISA sample holder. If desired the film may be exposed to generate substantially circular filters corresponding to the 12 columns and 8 rows of the sample plate permitting multiple filters for each optical density and color as well as two columns of zero optical density for each row of the photometer. Test results of high quality are thus easily obtained at minimal cost. The optical density of the first color is linearly increased by selectively increasing the length of time the film is exposed to produce the additional filters. The QC plate is thus highly accurate while also being extremely low in cost to produce as well as simple and rugged.

The signals generated by the detectors of the ELISA spectrophotometer using the QC plate are analyzed using algorithms written in the form of a software program and executed on an appropriate computer such as a microprocessor. These algorithms are designed to assure the integrity and consistency. The resulting output is a combined calibration and quality control analysis that instantly informs an operating technician whether the ELISA spectrophotometer is free of a large number of potential sources of error. The resulting output can be printed and retained to satisfy typical governmental regulatory requirements.

BRIEF DESCRIPTION OF THE DRAWINGS

FIG. 2 shows a top view of an embodiment of the present invention for an ELISA spectrophotometer;

FIG. 3 shows a cross section of an embodiment of the present invention; and

DETAILED DESCRIPTION

Figure 1:
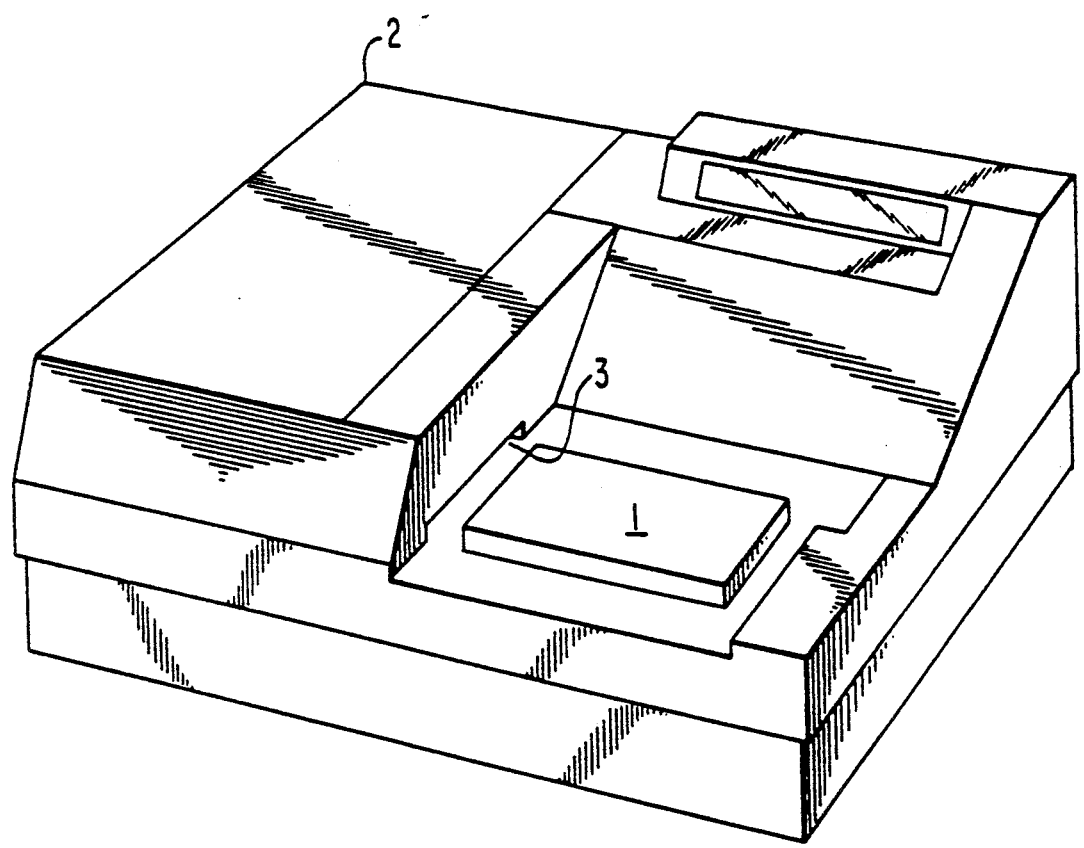
FIG. 1 shows an ELISA spectrophotometer.

FIG. 1 shows a conventional ELISA spectrophotometer, EAR 400 FW, manufactured by SLT Labinstruments G.m.b.H, of A-5082 Grodig/Salzburg, Austria. The sample holder 1 is shown in a position prior to being read by the ELISA spectrophotometer. For reading, the sample holder may be fed into the spectrophotometer through a slot 3.

FIG. 2 shows an enlarged view, from the top, of a piece of film, having a length and width about the same as the length and width of an ELISA sample holder. As shown in FIG. 2, the film has been selectively exposed, in the presence of a color filter, to comprise filters corresponding to a plurality of sample wells arranged in a matrix of 8 rows and 12 columns. Preferably, the filters are centered at the point corresponding to the center of each sample well in a standard ELISA sample holder. Also, preferably the diameter of the filters is approximately the same or smaller than the diameter of the sample well, however as will be obvious to those of ordinary skill in the art the filters may have a diameter larger than the diameter of the sample well in a standard ELISA sample holder. As will be also understood by those of ordinary skill in the art, the present invention includes embodiment wherein the film is selectively exposed to produce one or more filters in different size arrays.

The configuration of an 8×12 matrix is standard for an ELISA spectrophotometer. Columns 1 and 2 contain a zero optical density filter that can be produced most simply by not exposing that portion of the film. Columns 3-10 contain linearly increasing densities of the first color optical filter produced by increasing the exposure time of the film. Columns 11 and 12 contain filters of a second color.

FIG. 3 shows a cross section of the film shown in FIG. 2. As shown in FIG. 3, the film may be preferably enclosed in sheet of clear glass or plastic.

Figure 4:
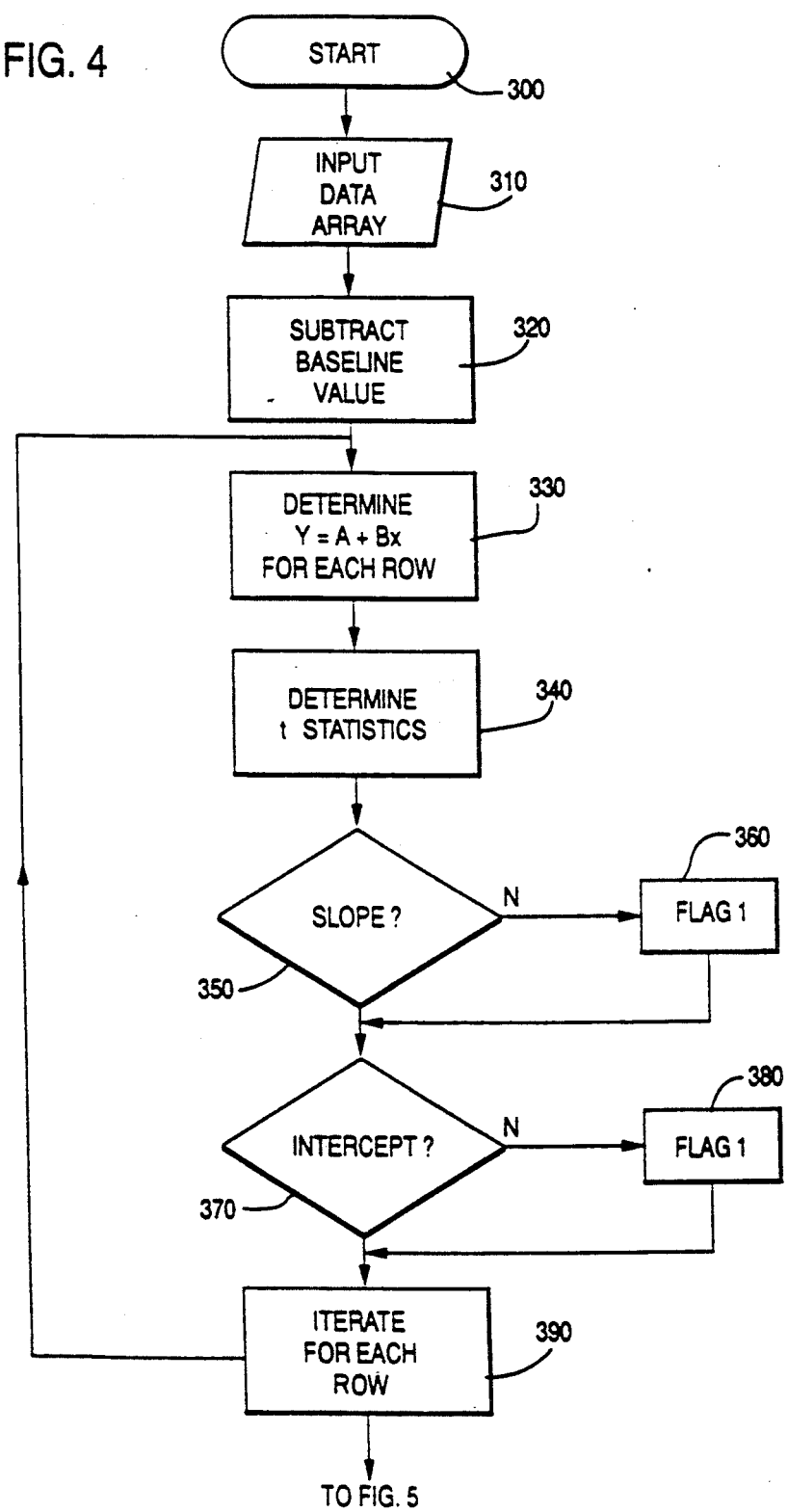
FIGS. 4-6 show a flow chart for analyzing the output of the spectrophotometer generated using an embodiment of the present invention such as depicted in FIG. 2.
Figure 5:
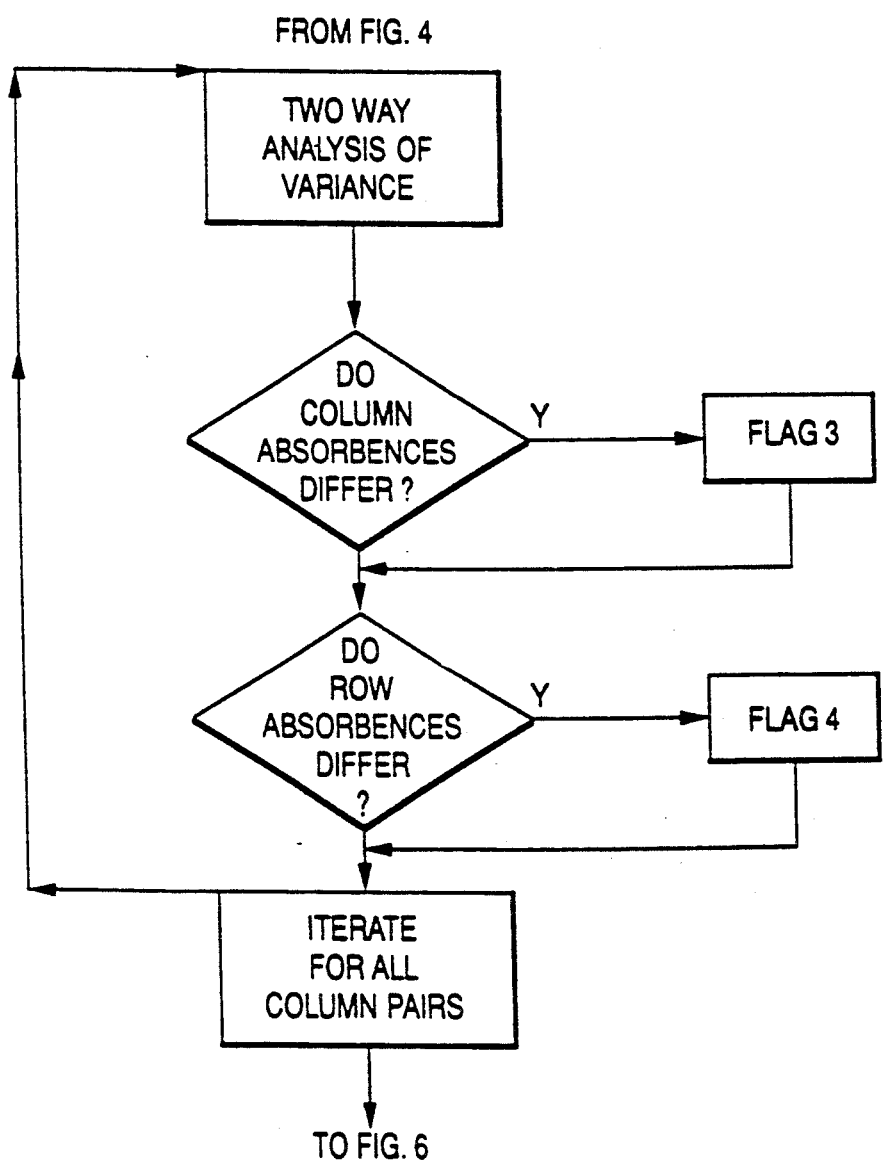
Figure 6:
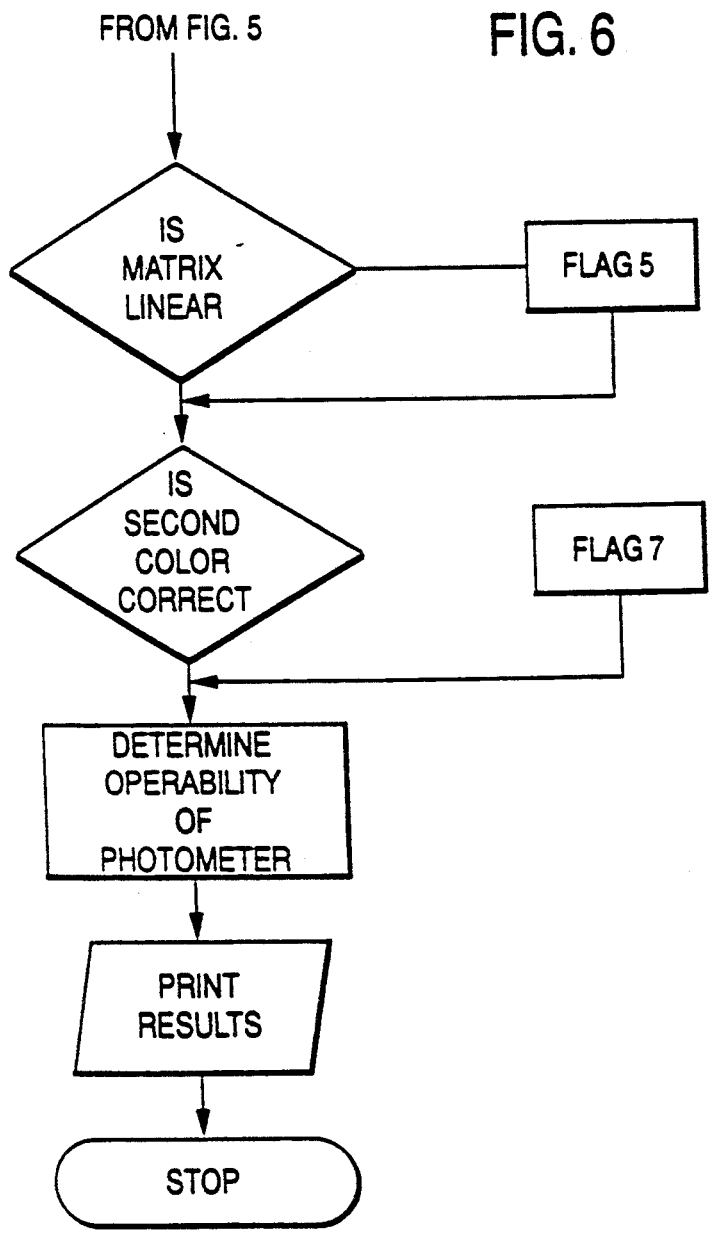

FIGS. 4-6 show the flow chart for the preferred analysis to be conducted on the output of the ELISA spectrophotometer using the QC plate shown in FIGS. 2 and 3. The flowcharts implement mathematical operations that are well known in the art as found in Walpole, et al., *Probability and Statistics for Engineer and Scientists*, McMillan, Inc. (1985), incorporated herein by reference.

Referring to FIG. 4, the program starts at step 300 and inputs an array of numbers at step 310. The array corresponds to the absorbance values obtained from each filter of the QC plate. The data is stored in a 96 element matrix for the embodiment of the present invention shown in FIG. 2. The absorbance values from the 16 elements in the first two columns is averaged and subtracted from each element in the matrix at step 320. This step constitutes the conventional baseline measurement used in prior art analysis routines.

The program of the present invention proceeds to determine a linear regression at step 330 for each row of the matrix, corresponding to at least one channel of the spectrophotometer. The values for the linearly increasing optical density filters are compared against a linear model in the form $Y = A + Bx$. A statistical determination of the slope for columns 1-10 of each row is computed at step 340. The comparison is performed for each row of the array having linearly increasing optical density filters. The necessary statistics are determined at step 340. These mathematical operations are known in the art and disclosed, for example, on pages 315-31 of Walpole, et al. Whether the slope corresponds to the known value is determined at step 350. If not, flag 1 is set at step 360. At step 370, the Y intercept is compared against its predetermined value of zero. At step 390 the process is reiterated for each row of the QC plate.

Referring to FIG. 5, a two way analysis of variance is conducted on the measurements from the zero optical density filters. The analysis of variance determination is known in the art as disclosed, for example, on pages 393-444 of Walpole, et al. The data for the zero density optical filters in the first column are analyzed to determine whether the average of the first column is significantly different than the average absorbence of the second column. If it is, then a defect exists and flag 3 is set. Then a determination of whether the average absorbence of any row in the first column pair is significantly different than the average absorbence of any other row in the first column pair is made. The significance test itself is known in the art as disclosed, for example, on pages 434-444 of Walpole, et al. If the average values are significantly different, the spectrophotometer is not operating correctly and flag 4 is set. The process is iterated for each column pair of the test data from the QC plate.

Figure 5A:
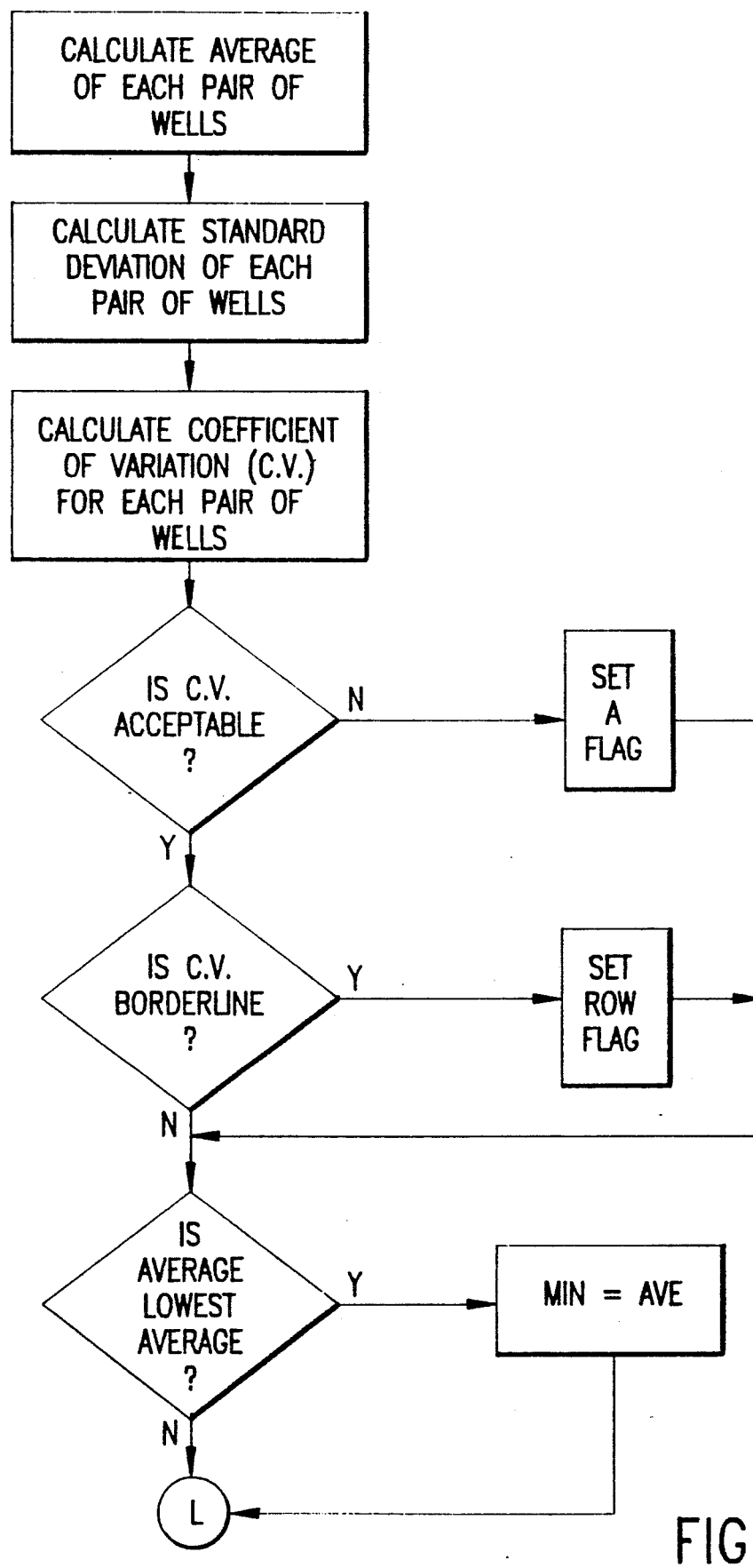
Figure 5B:
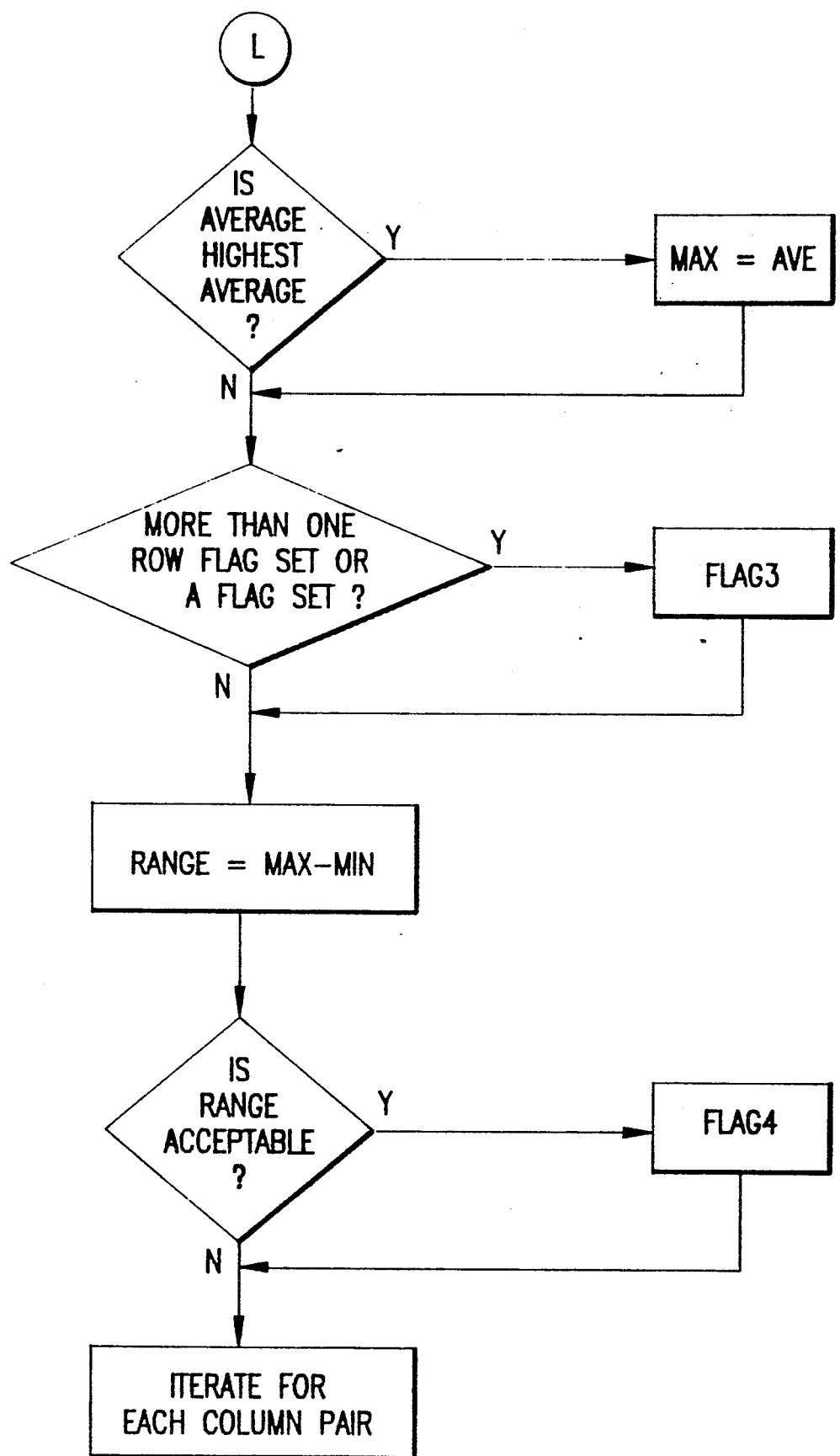

Alternatively, referring to FIGS. 5(a) and 5(b), a coefficient of variation (CV) check and a range check are performed on the measurements from the zero optical density filters. The data for each pair of wells is analyzed to calculate the average of the pair of wells and the coefficient of variation for the wells. Based on pre-established limits for acceptable CV and borderline CV, flags are set to indicate the number of pairs of wells that are unacceptable and the number of pairs of wells that are borderline. If one or more pairs of wells are unacceptable or, two or more pairs of wells are borderline, then a defect exists and flag 3 is set. From the average values calculated, a range is determined. If the range is wider than a pre-established limit, then a defect exists and flag 4 is set. The process is iterated for each column pair of the test data from the QC plate.

Referring to FIG. 6, a conditional step determines whether the absorbance values from the linearly increasing optical density filters really do increase linearly using an analysis of variance on a linear regression model for rows 1-8 and columns 1-10. If not, the spectrophotometer is not operating properly and a flag 5 is set. A non-linear operation of the photometer indicates that it is not operating properly because the QC plate should generate a linear response. Finally, whether the average absorbence values obtained using the second color optical density filter is significantly different from a predetermined standard absorbence value is determined. If there is a significant difference, the spectrophotometer is not operating properly and flag 7 is set. Flags 1-7 are analyzed. An output is generated to indicate whether the photometer is operational. If any of flags 1-7 are set, the output will indicate that the photometer is not operational. Further, the flags 1-7 can be used to generate diagnostic codes to help in determining the source of error in the spectrophotometer.

The foregoing program can be implemented on a standard personal computer. The PC receives its input directly from the spectrophotometer and generates its output using a standard printer. The use of a PC to control an ELISA spectrophotometer is well known in the art.

The foregoing QC plate has numerous advantages over the prior art. Specifically, the sample wells of the QC plate correspond in number and location to those used to make laboratory observations. The ability of the spectrophotometer to position the QC plate is thus checked along with the additional electrical and optical error sources noted in the background to this invention. The accuracy of the calibration and quality assurance check obtained with the ELISA spectrophotometer thus have the accuracy and stability over time normally expected of a clinical laboratory.

EXAMPLE

An apparatus for the calibration and quality assurance of a multichannel spectrophotometer, according to the present invention may be produced as follows.

A piece of color slide film, having a length and width roughly approximating the length and width of a standard ELISA sample well plate, is placed in a holder which will allow the film to be exposed to light.

A mask, formed of a material which blocks the transmission of light, is prepared. The mask has a plurality of substantially circular holes, having a center corresponding to the center of the sample wells in a standard ELISA sample well plate, arranged in an row by 12 column matrix corresponding to the 8 by 12 matrix of a standard ELISA sample well plate. The mask also has means for selectively blocking all or part of the matrix of holes.

The mask is placed over the film in a manner wherein the means for selectively blocking all or part of the matrix of holes in the mask may be manipulated to allow light to pass through all or part of the holes in the matrix to expose portions of the film.

The mask and film are then placed in a chamber, or dark room, wherein the mask and film may be exposed to colored light. To produce an apparatus for the calibration and quality assurance of a multichannel spectrophotometer the blocking means on the mask are moved to expose 2 columns of holes in the 8 by 12 matrix. The mask and film are then exposed to color light for a fixed time period. The blocking means on the mask are then moved to expose an additional 2 columns of holes in the 8 by 12 matrix. The mask and film are then re-exposed to the colored light for an additional time period. Thus, portions of the film corresponding to the first 2 columns of holes in the mask, are exposed twice and portions of the film corresponding to the second 2 columns of holes in the mask are exposed once, thereby creating 2 columns of darker filters on the film and 2 columns of lighter filters on the film. The blocking means on the mask are then moved again to expose an additional 2 columns of holes in the 8 by 12 matrix and the mask and film are re-exposed to color light for an additional time period. This step is repeated until 10 columns of filters are created on the film, with each set of 2 columns being exposed to the color light for a decreasing exposure time. The portion of the film corresponding to the last 2 columns of the 8 by 12 matrix is not exposed to the colored light so that clear filters are produced. The film corresponding to the last 2 columns may be reversed masked to produce substantially circular clear filters corresponding to the last 2 columns of the 8 by 12 matrix of sample wells in a standard ELISA sample well plate.

In this fashion an apparatus for the calibration and quality assurance of a multichannel spectrophotometer is created having an 8 by 12 matrix of filters corresponding to the 8 by 12 matrix of sample wells in a standard ELISA spectrophotometer sample well plate.

By a similar method, the film corresponding to two columns of the 8 by 12 matrix may be exposed to a light of a different color to produce an apparatus according to the present invention having filters of two different colors.

The film thus produced may be encased in clear plastic for protection or used as a "master" to produce additional apparatus for the calibration and quality assurance of a multichannel spectrophotometer.

The principles, preferred embodiments and modes of operation of the present invention have been described in the foregoing specification. The invention which is intended to be protected herein should not, however, be construed as limited to the particular forms described as these are to be regarded as illustrative rather than restrictive. Variations and changes may be made by those skilled in the art without departing from the spirit of the invention. Accordingly, the foregoing detailed description should be considered exemplary in nature and not as limiting to the scope and spirit of the invention set forth in the appended claims.

What is claimed is:

1. A quality monitoring apparatus for a photometer used to sample a plurality of samples, the photometer having at least one light source and at least one detector for generating signals corresponding to light from the samples, the quality monitoring apparatus comprising:
a sheet of photographic film having at least one filter having an optical density of a known value and a first color and corresponding to an area of the film that has been selectively exposed, each filter being positioned at a location at which the photometer samples one of the plurality of samples.

2. The quality monitoring apparatus of claim 1 wherein the sheet of film further comprises: a plurality of said filters each filter having an optical density of a known value which si the same or different than other filters and a first color, and wherein the filters are positioned at more than one location at which the photometer samples one of the plurality of samples.

3. A quality monitoring apparatus as claimed in claim 2, wherein the film further comprises filters having a second color.

4. A quality monitoring apparatus as claimed in claim 2, wherein the filters are arranged in an eight row by twelve column matrix comprising two columns each of: zero optical density filters, second color filters and each of four different optical densities of the first color filters.

5. A quality monitoring apparatus as claimed in claim 4, wherein the four different optical densities of the filters of the first color increase linearly sequentially.

6. A quality monitoring apparatus as claimed in claim 5, wherein the linear increase in the optical density of the filters is obtained by increasing the time of exposure of the film.

7. The quality monitoring apparatus of claim 2 wherein the outside dimensions of the sheet of film substantially correspond to outside dimensions of a standard ELISA spectrophotometer sample well plate.

8. The quality monitoring apparatus of claim 4 wherein each filter in the matrix of filters corresponds in location to the 8 by 12 matrix of positions at which the photometer samples one of sample wells in a standard ELISA spectrophotometer sample well plate.

9. The quality monitoring apparatus of claim 5 wherein each filter in the matrix of filters corresponds in location to the 8 by 12 matrix of positions at which the photometer samples one of the sample wells in a standard ELISA spectrophotometer sample well plate.

10. The quality monitoring apparatus of claim 9 wherein the outside dimensions of the sheet of film substantially correspond to outside dimension of a standard ELISA spectrophotometer sample well plate.

11. The quality monitoring apparatus of claim 10 further comprising two sheets of clear plastic, each having outside dimensions that substantially correspond to outside dimensions of a standard ELISA spectrophotometer sample well plate and wherein the film is disposed between said two sheets.

12. A quality monitoring apparatus as claimed in claim 2 wherein the filters are arranged in an eight row by twelve column matrix comprising two columns of zero optical density filters, two columns of the first color filters at a first optical density, two columns each of the first color filters at three different optical densities, different from the first optical density, and two columns of second color filters.

13. The quality monitoring apparatus as claimed in claim 12 wherein the four different optical densities of the filters of the first color increase linearly sequentially.

14. The quality monitoring apparatus of claim 12 wherein each filter in the matrix of filters corresponds in location to the 8 by 12 matrix of position at which the photometer samples one of the sample wells in a standard ELISA spectrophotometer sample well plate.

15. The quality monitoring apparatus of claim 13 wherein each filter in the matrix of filters corresponds in location to the 8 by 12 matrix of positions at which the photometer samples one of the sample wells in a standard ELISA spectrophotometer sample well plate.

16. The quality monitoring apparatus of claim 14 wherein the outside dimensions of the sheet of film substantially correspond to the outside dimensions of a standard ELISA spectrophotometer sample well plate.

17. The quality monitoring apparatus of claim 16 further comprising two sheet of clear plastic, each having outside dimensions that substantially correspond to outside dimensions of a standard ELISA spectrophotometer sample well plate and wherein the film is disposed between said two sheets.

18. The quality monitoring apparatus of claim 15 wherein the outside dimensions of the sheet of film substantially correspond to the outside dimensions of a standard ELISA spectrophotometer sample well plate.

19. The quality monitoring apparatus of claim 18 further comprising two sheet of clear plastic, each having outside dimensions that substantially correspond to outside dimensions of a standard ELISA spectrophotometer sample well plate and wherein the film is disposed between said two sheets.

* * * * *